(12) United States Patent
Mori et al.

(10) Patent No.: US 7,018,345 B2
(45) Date of Patent: Mar. 28, 2006

(54) IONTOPHORESIS SYSTEM

(75) Inventors: Kenji Mori, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 10/727,582

(22) Filed: Dec. 5, 2003

(65) Prior Publication Data

US 2004/0116964 A1   Jun. 17, 2004

(30) Foreign Application Priority Data

Dec. 6, 2002  (JP)  ............................. 2002-356075

(51) Int. Cl.
*A61B 5/00* (2006.01)
(52) U.S. Cl. .................... 600/573; 600/386; 604/20
(58) Field of Classification Search ............ 604/20–21; 600/362, 573, 579, 368, 349; 607/149
See application file for complete search history.

(56) References Cited

U.S. PATENT DOCUMENTS

| | | | | |
|---|---|---|---|---|
| 569,380 | A * | 10/1896 | Hollingsworth | 604/20 |
| 5,279,543 | A * | 1/1994 | Glikfeld et al. | 604/20 |
| 6,059,736 | A * | 5/2000 | Tapper | 600/573 |
| 6,219,574 | B1 * | 4/2001 | Cormier et al. | 604/20 |
| 6,308,104 | B1 * | 10/2001 | Taylor et al. | 607/118 |
| 6,391,643 | B1 * | 5/2002 | Chen et al. | 436/14 |
| 6,505,069 | B1 * | 1/2003 | Scott et al. | 604/20 |
| 6,553,255 | B1 * | 4/2003 | Miller et al. | 604/20 |

FOREIGN PATENT DOCUMENTS

| | | |
|---|---|---|
| EP | 1082940 A1 | 3/2001 |
| WO | WO 96/00110 | 1/1996 |

* cited by examiner

*Primary Examiner*—Mark Bockelman
(74) *Attorney, Agent, or Firm*—Townsend & Banta

(57) ABSTRACT

The present invention provides an iontophoresis system for non-invasively taking a physiological substance out of the living body, the system being suitably used for the mucous membrane. The present iontophoresis system non-invasively takes a physiological substance out of a living body. The system includes a plurality of electrode structures and a power supply device connected to the electrode structures. At least one of the electrode structures has a physiological substance extraction pad applied to the mucous membrane. In the present system, the time to apply electric energy to the living body by the power supply device is set between 30 seconds and 20 minutes. The physiological substance extraction pad which is provided in the electrode structure is applicable to the mucous membrane of the mouth and can be used, for example, to monitor glucose in the living body or an amount of drug administered.

10 Claims, 3 Drawing Sheets

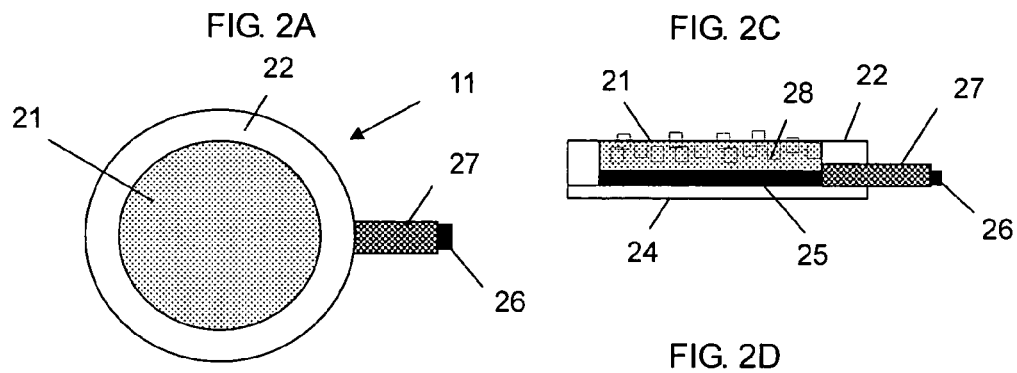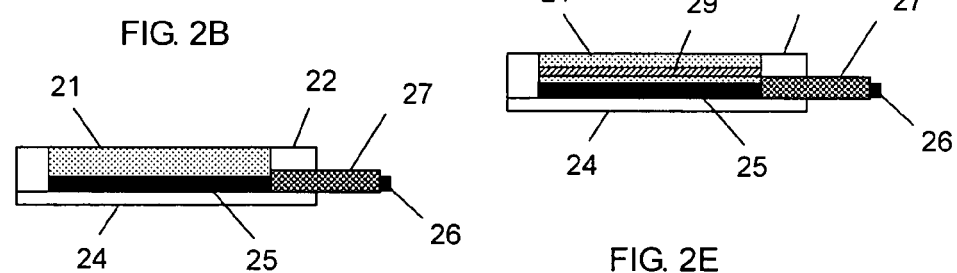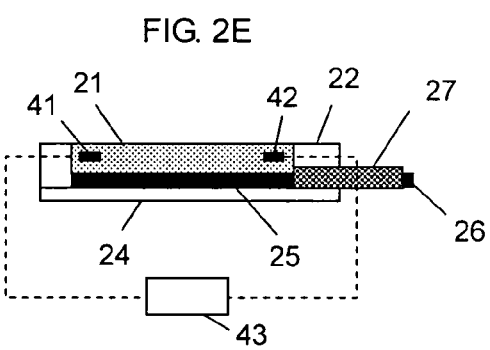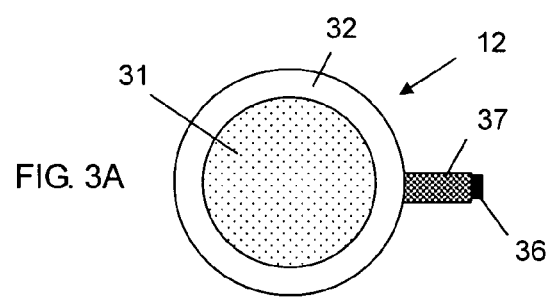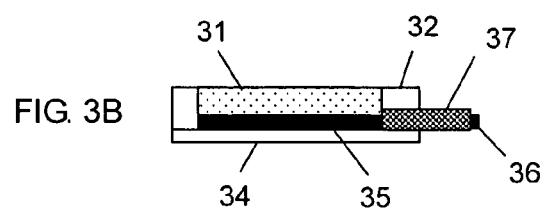

IONTOPHORESIS SYSTEM

BACKGROUND OF THE INVENTION

1. Field of the Invention

The present invention relates to an iontophoresis system for non-invasively taking a physiological substance out of a living body.

2. Description of the Related Art

A method has hitherto been known which externally and non-invasively diagnoses a living body using a supersonic wave, CT scanning, an X ray, or the like. A method has also been widely used which invasively takes out blood to measure an enzyme, protein, sugar, lipid, antibody, antigen, or the like contained in the blood. However, since this method is invasive, a patient may feel pain when pricked with a needle or the site pricked with the needle may later be infected.

On the other hand, for example, WO 96/00110 1 discloses a system that utilizing iontophoresis to non-invasively measure the level of glucose in the living body.

With this system, an electrode is stuck to the skin, and a current is conducted to the electrode to cause the flow of ions or water through the passage of the electrode—the skin—the interior of the living body—the skin—the electrode. Then, this flow is utilized to take glucose out of the living body, and its amount is measured. This system allows the diabetes to be diagnosed and also allows the blood sugar level to be monitored. In this case, the electrode may be stuck to the mucous membrane of the mouth or the like in place of the skin. Furthermore, when this system comprises a sensor device, it can detect or quantify an extracted substance.

Furthermore, EP 1 082 940 A1 discloses an iontophoresis device structure and a method of detecting a physiological substance.

This system comprises an applicator having a detecting member configured to utilize iontophoresis to adsorb a physiological substance. This system is applied to the skin or the mucous membrane and uses an immunological or chemical method to detect a physiological substance moved as a result of iontophoresis. With this method, by processing the detecting member to which the physiological substance has been adsorbed, qualitative measurements can be carried out on the basis of, for example, the depth of the color of the stained cells and their number.

BRIEF SUMMARY OF THE INVENTION

The skin does not only have a barrier function of preventing the invasion of foreign bodies but also serves to prevent the volatilization of moistures in the living body. Consequently, components cannot be sufficiently extracted from the living body using non-invasive physiological substance measuring equipment applied to the skin. Such equipment is likely to make measurement errors and may not be sensitive enough. The above document states that the iontophoresis system is applicable not only to the skin but also to the mucous membrane. However, it does not illustrate any system structures that are particularly suitable for applications to the mucous membrane. Compared to applications to the skin, heavy burdens are imposed on a patient when the iontophoresis electrode is stuck to the mucous membrane of his or her mouth or the like. For practical reasons, it is desirable to reduce these burdens.

It is thus an object of the present invention to provide an iontophoresis system for non-invasively taking a physiological substance out of the living body, the system being suitably used for the mucous membrane.

This object is accomplished using an iontophoresis system for non-invasively taking a physiological substance out of a living body, the system comprising a plurality of electrode structures and a power supply device connected to the electrode structures, the system being characterized in that at least one of the electrode structures has a physiological substance extraction pad applied to a mucous membrane, and a time to apply electric energy to the living body by the power supply device is set between 30 seconds and 20 minutes. Here, the electrode structure having the physiological substance extraction pad may comprise an ion exchange resin or an ion exchange membrane. Furthermore, the electrode structure having the physiological substance extraction pad may comprise a device quantifying the physiological substance or a device qualitatively measuring the physiological substance. The physiological substance may be a drug administered for treatment.

Furthermore, the iontophoresis system of the present invention comprises two electrode structures, fixing members fixing the electrode structures, a spring member provided between the fixing members arranged to rotatably cross each other, and a power supply device connected to the electrode structures, wherein at least one of the electrode structures has a physiological substance extraction pad applied to a mucous membrane. One of the electrode structures may be provided for the mucous membrane of the mouth and the other may be provided for the skin.

Moreover, according to the present invention, there is provided a method of analyzing a physiological substance for using iontophoresis to non-invasively take a physiological substance out of a living body for analysis, the method comprising applying a physiological substance extraction pad to a mucous membrane, applying electric energy to the living body via the pad for 30 seconds to 20 minutes by the iontophoresis, and quantifying or qualitatively measuring a physiological substance extracted in the pad. Here, the physiological substance extraction pad may be applied to a mucous membrane of a mouth. The physiological substance extraction pad may be used to, for example, extract glucose.

These arrangements provide an iontophoresis system for non-invasively taking a physiological substance out of the living body and for quantitatively or qualitatively evaluating thereof, the physiological substance including a component (substance) born of a living body, a drug administered to a living body, etc., and the system being suitably used for the mucous membrane, particularly, the mucous membrane of the mouth.

BRIEF DESCRIPTION OF THE DRAWINGS

FIGS. 2A–2E are schematic views showing examples of an electrode structure applied to the mucous membrane of the mouth, FIG. 2A being a plan view, FIG. 2B being a sectional view and FIGS. 2C–2E being other sectional views;

FIGS. 3A–3B are schematic views showing an example of an electrode structure applied to the skin, FIG. 3A being a plan view, and FIG. 3B being a sectional view;

DETAILED DESCRIPTION OF THE PREFERRED EMBODIMENTS

Figure 1:
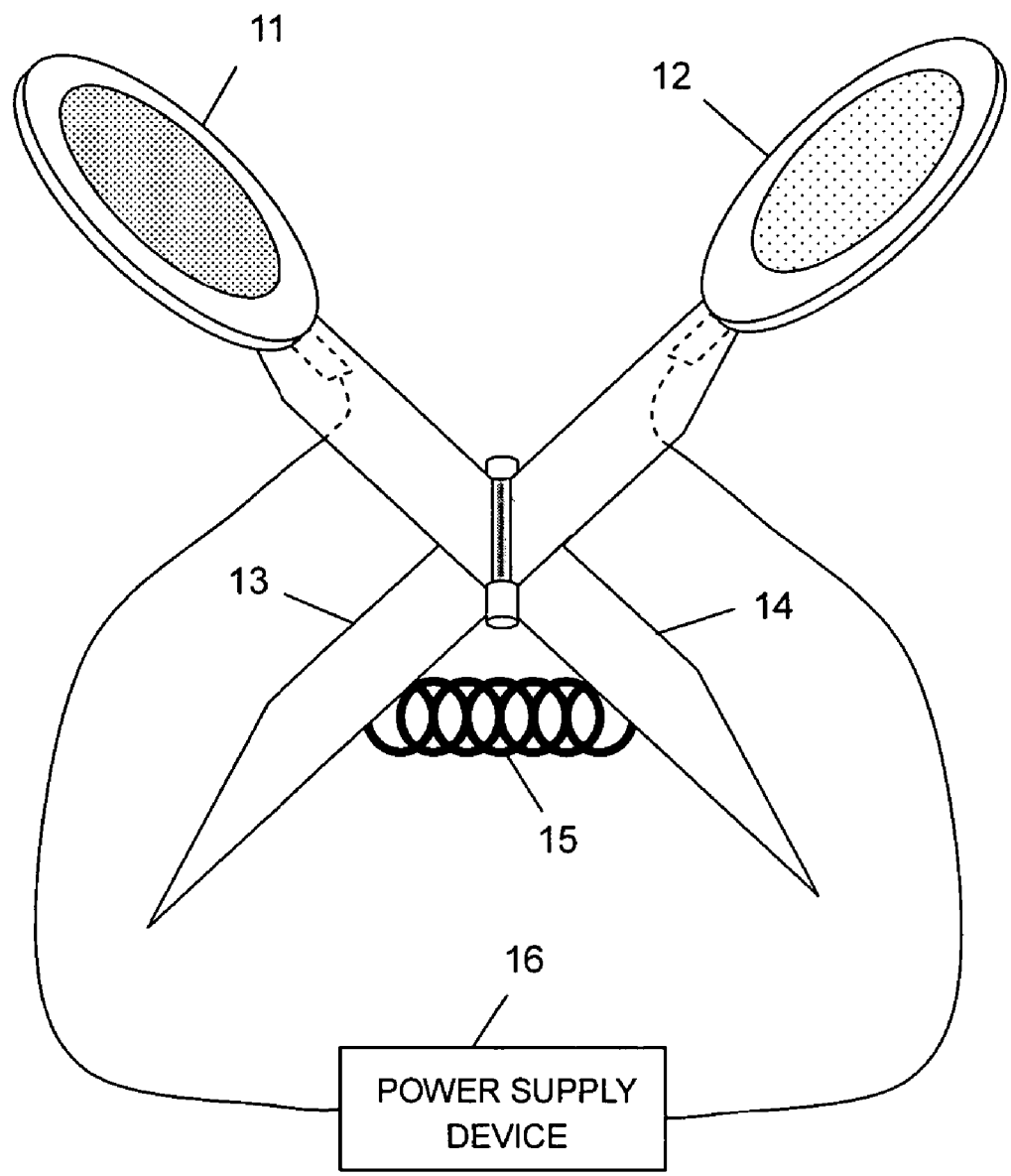
FIG. 1 is a view showing an embodiment of an iontophoresis system according to the present invention.

FIG. 1 is a view showing an embodiment of an iontophoresis system according to the present invention. The present system comprises an electrode structure 11 applied to the mucous membrane of the mouth, an electrode structure 12 applied to the skin, fixing members 13 and 14 that fix the respective electrode structures, a spring member 15 provided between the fixing members arranged to rotatably cross each other, and a power supply device 16 connected to the electrode structures 11 and 12.

FIGS. 2A–2E are schematic views showing examples of the electrode structure 11 applied to the mucous membrane of the mouth. FIG. 2A is a plan view, FIG. 2B is a sectional view and FIGS. 2C–2E are other sectional views. The electrode structure 11, as shown in FIGS. 2A and 2B, comprises an extraction pad 21 that extracts a physiological substance or in vivo component, a ring portion 22 that surrounds the extraction pad, a support 24 that supports the extraction pad and the ring portion, an electrode portion 25 arranged between the extraction pad and the support, and an electrode terminal 26 connected to the electrode portion. A physiological substance extracted from the mucous membrane is collected on the extraction pad 21. The ring portion 22 is required to reliably fix the extraction pad 21 so that it will not slip out. The electrode terminal 26 is integrated with the electrode portion 25, located immediately below the extraction pad. The electrode terminal 26 is covered with an insulator 27 except for its portion connected to the power supply device.

Materials for the extraction pad 21 include, for example, fibers such as a non-woven cloth, gauze, and absorbent cotton, agar, gelatin, a polyacrylic acid and its salt, polyvinylpyrrolidone and a copolymer of polyvinylpyrrolidone and vinyl acetate, a methyl cellulose and its derivative, pectin, a polyethylene oxide, a methylvinylether maleic anhydride copolymer, polyvinyl alcohol and its derivative or their saponifides, acrylic, asilicon-, SIS-, SBS-, urethane-, or natural rubber-based adhesive and their mixture, and these adhesive with the addition of a tackifier such as rosin, hydrogenated rosin, rosin ester, a terpene resin, a terpene phenol resin, a petroleum-based resin, a coumarone resin, or a coumarone-indene resin. However, the present invention is not limited to these materials. For these materials, an aqueous base is desirably used.

An ion exchange resin or membrane is preferably provided in the extraction pad 21 or at another appropriate position. In FIG. 2C, the ion exchange resin 28 is dispersed and/or mixed in the extraction pad 21. In FIG. 2D, the ion exchange membrane 29 is arranged parallel to the electrode portion 25 in the extraction pad 21. The ion exchange resin or membrane is provided in order to separate an extracted physiological substance from the electrode portion 25 because the contact of the extracted physiological substance with the electrode portion 25 may affect quantification. The ion exchange resin may be a cation exchange resin or an anion exchange resin.

The cation exchange resin may include, for example, Amberlite XT-1004, IR120B, IR-122, IR-124, 252, XT-1031, 200C, IRC-50, or IRC-76 (manufactured by ORGANO CORPORATION), Diaion SK-1B, SK-104, SK-110, PK-208, PK-216, WK-10, WK-11, or WK-20 (manufactured by MITSUBISHI CHEMICAL CORPORATION), Dowex HCR-S, HGR-W2, 88, or MWC-1H (manufactured by The Dow Chemical Company), Duolite C-20, C-26, C-264, C-3, C-433, or C-464 (manufactured by Rohm and Haas Co.), Imac C-12, C-16P, Z-5, GT-73, Lewatit S-100, SP-112, SP-120, S-109, or CNP-80 (manufactured by Bayer), or an inorganic ion exchanger, for example, Bio-Rad ZP-1, ZM-1, ZT-1, AMP, KCF-1, HZO-1, or HTO-1 (manufactured by Bio-Rad), AMD-Erba, HMD-Erba, HAP-Erba, ZPH-Erba, TDO-Erba, COX-Erba, AAO-Erba, CUC-Erba, or CUS-Erba (manufactured by Carlo Erba), Zerwat, or Allasion Z (manufactured by Dia Prosim), Ionac C100, C101, C102, or M-50 (manufactured by Ionac. Chem. Comp.), Decalsco (F, Y), Zeo-Dur, or Zerolite green sand (manufactured by Permit), or IXE-300, IXE-400, IXE-100, IXE-500, or IXE-1000 (manufactured by TOAGOSEI CO., LTD.).

The anion exchange resin may include, for example, Amberlite IRA-400, IRA-401, IRA-402, IRA-420, XT-5007, IRA-900, IRA-904, IRA-938, IRA-458, IRA-958, IRA-410, IRA-411, IRA-416, IRA-910, IRA-68, or IRA-35 (manufactured by ORGANO CORPORATION), Diaion SA-10A, SA-11A, SA-12A, PA-306, PA-312, PA-318, SA-20A, SA-21A, PA-406, PA-412, or PA-418(manufactured by MITSUBISHI CHEMICAL CORPORATION), Dowex SBR, SBR-P, 11, MSA-1, SAR, MSA-2, 66, or WGR-2 (manufactured by the Dow Chemical Company), Duolite A-113 plus, A-147, A-161, A-132, A-116 plus, A-162, A-368, or A-7 (manufactured by Rohm and Haas Co.), Imac A-34, A-33, A-31, A-32, A205, A-28, Lewatit M-500, MP-500, AP-247A, M-600, MP-600, MP-62, OC-1059, or CA-9222 (manufactured by Bayer), or cholestyramine. Any of these resins may be used for the present invention. Preferably, the anion exchange resin is used, and more preferably, the anion exchange resin containing chlorine ions, i.e. quaternary ammonium salt is used. Furthermore, a styrene, acrylic, or methacrylic polymer base is commonly used. However, the present invention is not limited to these polymer bases, and any polymer bases may be used provided that they are compatible with the ion exchange resin. Moreover, either a meltable or refractory resin may be used provided that it provides appropriate functions.

The ion exchange membrane may be either a cation or anion exchange membrane. The cation exchange membrane is, for example, a copolymer of divinylbenzene and styrene containing a sulfone group. The anion exchange membrane is, for example, a copolymer of divinylbenzene and styrene containing an amino group.

The electrode structure 11 may comprise a device that quantifies a physiological substance or a device that qualitatively measures a physiological substance. The device that quantifies a physiological substance is, for example, a glucose sensor. The device that qualitatively measures a physiological substance is, for example, a general antigen and antibody sensor.

In FIG. 2E, a glucose sensor is provided in the electrode structure applied to the mucous membrane of the mouth. The glucose sensor comprises at least two electrode 41, 42 and a detector connected between the electrodes. Glucose oxidase (GO) is fixed on the surface of one (for example, electrode 41) of the two electrodes 41 and 42. When energization is made by the iontophoresis system during the predetermined time, glucose (G) is extracted from the mucous membrane of the mouth in the extraction pad 21. Here, the glucose is oxidized by catalysis of the glucose exidase at the electrode 41 fixing the glucoseoxidase, as a result of which electrons are produced. The glucose can be quantified by the detector 43 detecting them as a potential difference between the electrodes 41 and 42. The detector 43 includes circuits for amplification of the potential difference, calculation, display, etc. These circuits may be mounted on a common substrate to the power supply device 16. Furthermore, the antigen and antibody sensor can be constructed similar to the glucose sensor.

The current density of an applied current for iontophoresis used as electric energy is 0.01 to 2 $mA/cm^2$, preferably 0.05 to 1 $mA/cm^2$ in terms of extraction efficiency and a current-induced stimulus to the skin. In this case, an applied voltage is 50 V or less, preferably 20 V or less, more preferably 10 V or less. A conduction pattern used is not particularly limited but may be a DC, a pulse, or pulse depolarization. A material for the electrode portion is not particularly limited but may be platinum, gold, carbon, or the like. A positive electrode may be composed of silver, while a negative electrode may be composed of silver/silver chloride. The material for the electrode portion is desirably carbon in terms of costs. Silver or silver/silver chloride is desirable in that its pH does not change even with conduction.

FIGS. 3A–3B is a schematic view showing an example of the electrode structure 12 applied to the skin. FIG. 3A is a plan view, and FIG. 3B is a sectional view. The electrode structure 12 comprises a counter pad 31 paired with the extraction pad 21, a ring portion 32 that surrounds the extraction pad, a support 34 that supports the counter pad and the ring portion, an electrode portion 35 arranged between the counter pad and the support, and an electrode terminal 36 connected to the electrode portion. The electrode terminal 36 is covered with an insulator 37.

A material for the counter pad 31 may be similar to that in the electrode structure 11 applied to the mucous membrane of the mouth. Also in this case, an aqueous base is desirably used.

The present iontophoresis system is operated as described below. In FIG. 1, the ends of the fixing members 13 and 14 are opened against the tensile force of the spring member 15. Correspondingly, the spacing between the electrode structures 11 and 12 is enlarged. Thus, the electrode structure 11 is brought to the mouth, while the electrode structure 12 is brought to the cheek. Both electrode structures are then fixed using the tensile force of the spring member 15 so that the cheek is sandwiched between these electrode structures. In this case, the electrode structure 11 is applied to the mucous membrane of the mouth, while the electrode structure 12 is applied to the skin of the cheek. Subsequently, the power supply device 16 is activated to apply electric energy to the living body via the electrode structures 11 and 12. Description will be given later of the time required by the power supply device 16 to apply electric energy. Electric energy is applied for a predetermined time. Then, the power supply device 16 is deactivated, and the iontophoresis system is removed from the living body. Subsequently, the physiological substance collected in the extraction pad 21 is analyzed. A method for measuring the extracted physiological substance is not particularly limited. However, the physiological substance can be measured using enzyme-induced reaction or electrochemically. Such a measuring device may be installed in the extraction pad or arranged outside it.

The physiological substance extracted as a result of iontophoresis is desirably ionic. However, the present invention is not limited to this aspect. The physiological substance or biocomponent is extracted as water resulting from conduction flows provided that it dissolves in water. Accordingly, glucose or the like can be extracted. In particular, it is essential for diabetes patients to frequently measure glucose. Thus, the system according to the present invention is very useful.

Furthermore, the measurement of a blood concentration of a physiological substance may be necessary not only to a substance born of a living body for diagnosis but also to a drug (physiologically active substance) administered from outside of a living body or its metabolite. Actually, on the site of remedy, the measurement of a blood concentration after administering a drug, called as the TDM (therapeutic drug monitoring), is carrying out to a drug (physiologically active substance) which has a small difference between the blood concentration of effective medication of the drug (physiologically active substance) or its metabolite and the developing range of side effect. However, it was necessary to collect blood by pricking with a needle to measure a blood concentration of a drug or the like in the blood. It is heavy burdens for a patient that this is frequently carried out. The present invention provides an effective method for avoiding the burdens to the patient, so that the drug or the like in the living body is extracted without pricking with a needle.

The drug, on which the TDM is carried out by the system of the present invention, may include, for example, antiepileptic such as ethosuximide, carbamazepine, clonazepam, diazepam, nitrazepam, sodium valproate, phenytoin, Phenobarbital, primidon, etc., psychopharmaceuticals such as chlorpromazine, haloperidol, etc., antidepressant such as amitriptyline hydrochloride, imipramine hydrochloride, maprotiline hydrochloride, etc., antimanic drugs such as lithium carbonate, etc., bronchodilator such as aminophyline, cholinetheophyline, theophyline, etc., cardiac glycoside such as digoxin, digitoxin, etc., antiarrhythmic drugs such as aprindine, quinidine, disopyramide, procainamide, mexiletine, lidocaine, etc., antibiotics such as amikacin sulfate, gentamicin sulfate, tobramycin, etc., immunosuppressant drugs such as cyclosporin, etc., antipyretic, analgesic, antiphlogistic drugs such as aspirin, etc., antithrombolytics such as Human Antithrombin III concentrated, dipyridamole, ticlopidine, heparin sodium, etc. The present invention can be used for the measurement or prediction of the blood concentration of the drugs mentioned above, but it is not limited to these drugs.

If the application of iontophoresis to the skin is compared with the application of iontophoresis to the mucous membrane, the mucous membrane allows substances to pass through more easily than the skin. In an example in which calcitonin is used as a model compound, the mucous membrane has an absorptivity six times higher than that of the skin. This applies not only to the administration of drugs through the skin or the mucous membrane but also to the removal of a physiological substance from the skin or the mucous membrane. Specifically, if iontophoresis is used to conduct the same current, a larger amount of physiological substance can be taken out via the mucous membrane than via the skin. Measurement of the resistance of the skin and mucous membrane showed that the skin offered a 4.5 times higher resistance than the mucous membrane. Thus, given the same voltage upper limit, the mucous membrane can be provided with a 4.5 times higher current than the skin. That is, by changing the takeout side from the skin to the mucous membrane, the conduction time can be reduced and the accuracy improved in connection with the difference in transmittance and resistance as described above. Even if a physiological substance is taken out via the skin, a certain amount of physiological substance can be taken out and quantified with 15 minutes of conduction. The amount of physiological substance that can be taken out increases consistently with the conduction time. However, by using the mucous membrane as an applied site as in the case with the present iontophoresis system, the conduction time can be reduced to one minute or shorter as described below.

As described above, it takes 15 minutes to take a physiological substance via the skin, and the skin offers a 4.5 times higher resistance than the mucous membrane. Furthermore, the mucous membrane has an about 6 times higher absorptivity than the skin. Consequently, the time required for extraction via the mucous membrane is:

15×60/(4.5×6)=33.333 . . . (about 30 seconds)

Thus, with the present iontophoresis system applied to the mucous membrane, electric energy must be applied for at least 30 seconds.

On the other hand, since the present iontophoresis system is applied to the mucous membrane, particularly the mucous membrane of the mouth, higher effects can be produced with a shorter application time. Thus, a preferable application time was examined by comparing the current invasive measuring method of using a needle to collect blood with the system applied to the mucous membrane of the mouth. As shown in the examples described later, with at most 20 minutes of application, many patients commented that the present system was similar to the current invasive measuring method or was better than the invasive measuring method but the application time must be reduced (easier to use, but not to be effective). All comments considered, it was determined that with this application time, the present system is slightly better than the current invasive measuring method. With at most 15 minutes of application, half of the patients commented that the present system was better than the invasive measuring method but the application time must be reduced (easier to use, but not to be effective). That is, with this application time, the present system is more excellent than the current measuring method. Furthermore, with at most 10 minutes of application, some commented that the present system was more excellent and more easier to use than the invasive measuring method". That is, with this application time, the present system is much more excellent than the invasive measuring method. When the application time was reduced to 5, 2, and 1 minute, more and more patients commented that the present system was more excellent than the current method. This indicates that the present system is much more excellent than the current method. Furthermore, for the use outside the patients' homes, all the patients used the system for at most 5 minutes. The application time was desirably at most 2 minutes, more desirably at most 1 minute. That is, the application time is desirably at most 20 minutes, preferably at most 10 minutes, more preferably at most 5 minutes, much more preferably 2 minutes, most desirably at most 1 minute.

EXAMPLES

Example 1

An iontophoresis system applied to the mucous membrane of the mouth and configured as shown in FIG. 1 was applied to 10 patients to examine an applicable time. In this case, the length of available application time was examined without actually conducting any currents. The iontophoresis system was compared with the currently most common measurement of glucose using invasive blood collection (conventional method) as an index of time.

Results of Example 1

The results are shown in Table 1.

TABLE 1

| Comparison with | Time for which the instrument must remain fixed | | | | | | |
|---|---|---|---|---|---|---|---|
| the current invasive blood collection | 30 min. | 20 min. | 15 min. | 10 min. | 5 min. | 2 min. | 1 min. |
| Invasive measuring method is better | 6/10 | 0/10 | 0/10 | 0/10 | 0/10 | 0/10 | 0/10 |
| Equivalent to the invasive measuring method | 4/10 | 8/10 | 5/10 | 1/10 | 0/10 | 0/10 | 0/10 |
| Better than the invasive measuring method but the application time must be reduced | 0/10 | 2/10 | 5/10 | 6/10 | 4/10 | 2/10 | 0/10 |
| More excellent than the invasive measuring method. Easier to use. | 0/10 | 0/10 | 0/10 | 3/10 | 6/10 | 8/10 | 10/10 |

As shown in Table 1, when the present system was applied for 30 minutes, 6 out of the ten patients felt that the application time was long and commented that the conventional method was more easy and convenient (the invasive measuring method is better). The remaining 4 patients commented that the present system was as easy to use as the conventional method (equivalent to the invasive measuring method) because they felt no pain in spite of the long application time. All comments considered, it was determined that the present system is not effective with 30 minutes of application. With 20 minutes of application, 8 patients felt that the present system was almost equivalent to the conventional method (equivalent to the invasive measuring method), and 2 commented that the present system was better than the conventional method (the invasive measuring method). Totally, it was determined that with this application time, the present system is slightly more excellent than the conventional method. Furthermore, with 15 minutes of application, half of the patients commented that the present system was equivalent to the conventional method, while the remaining half commented that the present system was superior to the conventional method. With 10 minutes of application, almost all patients commented that the present system was superior to the conventional method. With 5 minutes of application, 6 patients commented that the present system was more excellent and more easy to use than the conventional method. With 2 minutes of application, 8 patients made the same comment. With 1 minute of application, all of the 10 patients commented that the present system was more excellent and more easy to use than the conventional method.

Example 2

The application time was examined on the assumption that a system similar to that in Example 1 was used outside the patients' homes. The maximum length of time the patients tolerated the use of the present system outside their homes was examined. An appropriate application time was also examined.

Results of Example 2

The results are shown in Tables 2 and 3.

TABLE 2

| | Time for which the instrument must remain fixed | | | | | | |
|---|---|---|---|---|---|---|---|
| | 30 min. | 20 min. | 15 min. | 10 min. | 5 min. | 2 min. | 1 min. |
| The number of patients who will not use the system | 10/10 | 10/10 | 10/10 | 10/10 | 0/10 | 0/10 | 0/10 |
| The number of patients who will use the system | 0/10 | 0/10 | 0/10 | 0/10 | 10/10 | 10/10 | 10/10 |

TABLE 3

| | Patient | | | | | | | | | |
|---|---|---|---|---|---|---|---|---|---|---|
| | A | B | C | D | E | F | G | H | I | J |
| Presumably appropriate time | At most 2 min. | At most 1 min. | At most 1 min. | At most 1 min. | At most 1 min. | At most 1 min. | At most 1 min. | At most 1 min. | At most 1 min. | At most 1 min. |

As shown in Table 2, the maximum allowable time was 5 minutes. Moreover, as shown in Table 3, 1 patient commented that the desirable application time was at most 2 minutes, and 9 patients commented that it was at most 1 minute.

Example 3

Beagles were put under pentobarbital anesthesia. A positive electrode pad containing salmon calcitonin 1000 unit (an extraction pad of an electrode structure applied to the mucous membrane of the mouth) was applied to the mucous membrane of the mouth of each beagle. A negative electrode (a counter pad of an electrode structure applied to the skin) was applied to the ear of the beagle. A pulse depolarization type iontophoresis system was used to apply a 0.2-mA current for 30 minutes. Then, 30 minutes later, the level of salmon calcitonin in the blood was measured. An RIA kit (ROIK6003, Peninsula) was used for quantification.

Comparative Example 1

As in the case with Example 3, salmon calcitonin was administered to beagles under pentobarbital anesthesia. However, the positive electrode pad was not applied to the mucous membrane of the mouth but to the skin (belly). The negative electrode was applied to the ear. The other conditions are similar to those for Example 3.

Results of Example 3 and Comparative Example 1

Figure 4:
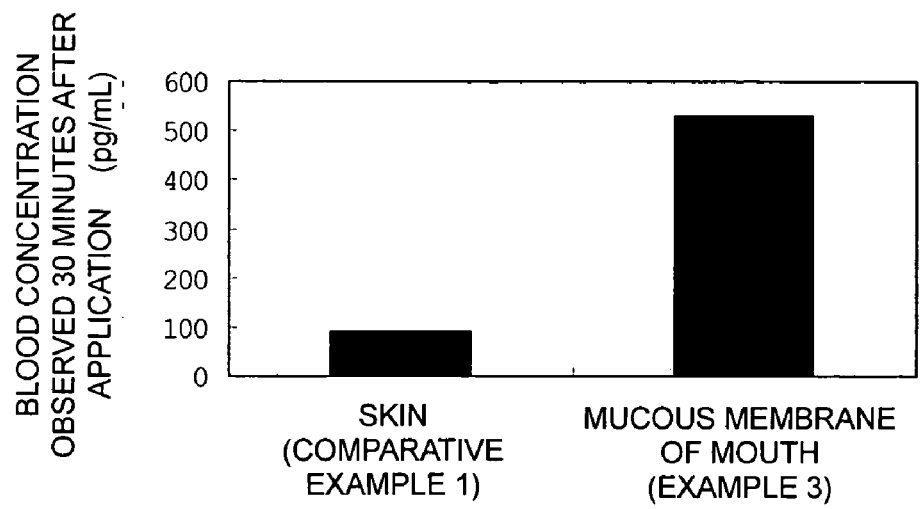
FIG. 4 is a graph showing a blood concentration observed 30 minutes after the present system has been applied to the mucous membrane of the mouth (Example 3) and to the skin (Comparative Example 1)

FIG. 4 is a graph showing the blood concentration observed 30 minutes after the application of the present system to the mucous membrane of the mouth (Example 3) and to the skin (Comparative Example 1). The blood concentration was about 530 pg/ml 30 minutes after salmon calcitonin was administered to the dog via the mucous membrane of the mouth (Example 3). The blood concentration was about 90 pg/ml 30 minutes after salmon calcitonin was administered to the dog via the skin (Comparative Example 1). Calcitonin is ionized, but owing to its large quantity, calcitonin permeates through the living body as a result of the flow of water caused by iontophoresis instead of its direct electric driving force. Therefore, in spite of a difference in direction, even a physiological substance such as glucose which is not ionized exhibits an about 6 times higher transmittance when it is transmitted (extracted) through the mucous membrane.

Example 4

A conductive gel was used to apply a 0.2-mA direct current to the mucous membrane of the mouth of each dog. The resulting resistance was measured.

Comparative Example 2

A conductive gel was used to apply a 0.2-mA direct current to the skin of each dog. The resulting resistance was measured.

Results of Example 4 and Comparative Example 2

Figure 5:
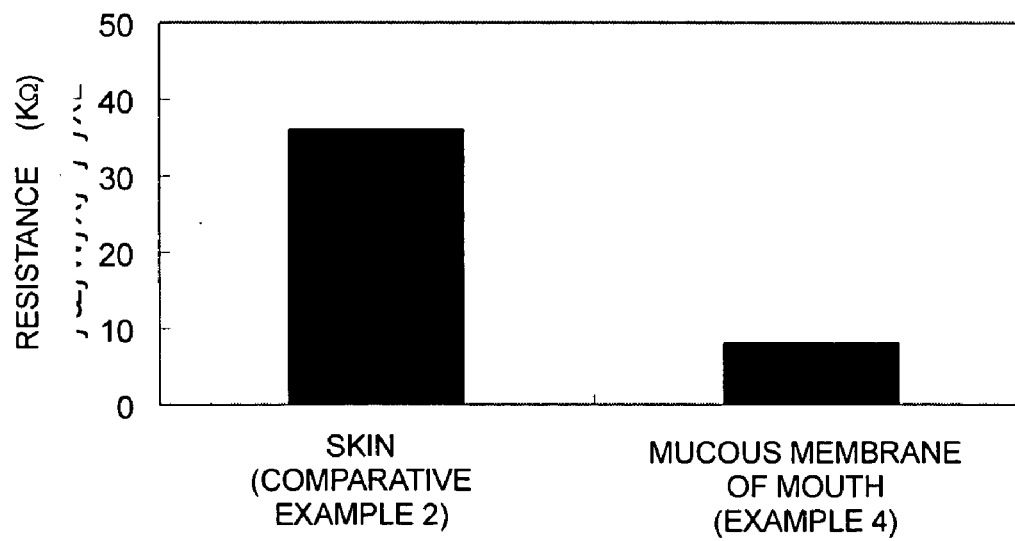
FIG. 5 is a graph showing the resistance of the mucous membrane of the mouth (Example 4) and of the skin (Comparative Example 2).

FIG. 5 is a graph showing the resistance observed when the current was applied to the mucous membrane of the mouth (Example 4) and to the skin (Comparative Example 2). In Example 4, the resistance of the mucous membrane of the mouth measured about 8 KΩ (kilo-ohm). In contrast, the resistance of the skin measured about 36 KΩ. Thus, the resistance of the skin was about 4.5 times higher than the resistance of the mucous membrane of the mouth. Consequently, if the present system is applied to the mucous membrane at the same voltage as that for the skin, a 4.5 times higher current can be applied to extract more of the physiological substance.

As described above, the present invention is a system for non-invasively taking out a physiological substance out of the living body for diagnosis. The present system uses electric energy to extract a physiological substance via the mucous membrane. In this case, the time required to apply electric energy for extraction is desirably about 30 seconds to 20 minutes, more desirably about 30 seconds to 15 minutes, more desirably about 30 seconds to 10 minutes, more desirably about 30 seconds to 5 minutes, more desirably about 30 seconds to 2 minutes, more desirably about 30 seconds to 1 minute. Electric energy is supplied using iontophoresis. The mucous membrane-applied pad of the iontophoresis system may contain the ion exchange resin or membrane. The ion exchange membrane may be the cation or anion exchange membrane, whereas the ion exchange resin maybe the cation or anion exchange resin. The iontophoresis system may contain the device that quantify or qualify a physiological substance. The extracted physiological substance is, for example, glucose. The physiological substance is preferably extracted from the mucous membrane of the mouth using the iontophoresis system.

Thus, the present invention provides an iontophoresis system for non-invasively taking a physiological substance out of the living body, the system being suitably used for the mucous membrane.

What is claimed is:

1. An iontophoresis system for non-invasively extracting a physiological substance out of a living body comprising:
    a first electrode structure having a physiological extraction pad thereon, said first electrode structure affixed to a first fixing member,
    a second electrode structure affixed to a second fixing member, said second fixing member hingedly engaged with said first fixing member at a hinge connection so as to form a cross shape,
    a spring member in attachment to the first fixing member and the second fixing member, on one side of the hinge connection, so as to bias the first electrode structure and the second electrode structure together, and
    a power supply device connected to the electrode structures.

2. The iontophoresis system according to claim 1, wherein one of the first electrode structures is provided for the mucous membrane of the mouth, and the second electrode structure is provided for the skin.

3. A method of analyzing a physiological substance using the iontophoresis system of claim 1 to non-invasively remove a physiological substance from a living body for analysis, comprising:
    applying the physiological substance extraction pad to a mucous membrane,
    applying electric energy of 10 volts or less to the living body via the pad for 30 seconds to 20 minutes by iontophoresis, and
    quantifying or qualitatively measuring a physiological substance extracted in the pad.

4. The method of analyzing a physiological substance according to claim 3, wherein the physiological substance extraction pad is used to extract glucose.

5. The method of analyzing a physiological substance according to claim 3, wherein the physiological substance extraction pad is adapted to be applied to a mucous membrane of a mouth.

6. The iontophoresis system according to claim 1, wherein the electrode structure having the first electrode further comprises a device quantifying the physiological substance or a device qualitatively measuring the physiological substance.

7. The iontophoresis system according to claim 1, wherein the physiological substance is a drug administered for treatment.

8. The iontophoresis system of claim 1, further comprising a glucose sensor in connection with the first and/or second electrode.

9. The iontophoresis system of claim 8, wherein the glucose sensor in connection with the first and/or second electrode comprises:
    a first sensor electrode,
    a second sensor electrode, and
    a detector conductively connecting the first sensor electrode and the second sensor electrode.

10. The iontophoresis system of claim 1, further comprising a general antigen and antibody sensor in connection with the first and/or second electrode.

* * * * *